United States Patent [19]

Ellison et al.

[11] Patent Number: Plant 5,546

[45] Date of Patent: Aug. 27, 1985

[54] ASPARAGUS PLANT-FEMALE PLANT NO. 53 INEZ

[75] Inventors: J. Howard Ellison, Milltown; John J. Kinelski, Princeton, both of N.J.

[73] Assignee: Rutgers University, New Brunswick, N.J.

[21] Appl. No.: 544,008

[22] Filed: Oct. 21, 1983

[51] Int. Cl.[3] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

An Asparagus Plant having predominately female characteristics, with resistance to rust (*Puccinia asparagi*), tolerance to root and crown rot (*Fusarium oxysporum*) and (*F. moniliforme*), vigorous through long life, having a largest stalk of 21.4 mm diameter, mean diameter of three largest stalks being 20.8 mm, an average of 26 stalks per plant and a stalk vigor index (No. X (Mean Diameter)$^2$) of 11,249.

2 Drawing Figures

This invention relates to a female asparagus plant which is one selected by us as a result of an intense and continuing program of development of asparagus, to improve resistance to disease and increase productivity.

The instant plant which is denoted in our records as No. 53, is also identified as "Inez" and was selected from a field of Mary Washington which has been grown for more than thirty five years, it is undoubtedly basically of that background being an unpatented variety, though differing in many respects.

We have asexually reproduced our variety "Inez" by crown division and also by tissue culture and find that it comes true in successive generations, with the characteristics of resistance to rust (*Puccinia asparagi*), tolerance to root rot (*Fusarium oxysporum*) and crown rot (*F. moniliforme*).

The fact that the female plant transmits the aforementioned characteristics makes the same valuable and it enables a farmer to grow hybrids of the variety where standard cultivars cannot be grown profitably.

It has also been found that our new variety is very long lived, having been found to be productive for about twenty years our program of development establishing that such life is measured in years and that this longevity is also transmitted to progeny along with the high yield capability as well as tolerance to fusarium and resistance to disease.

The initial growth of the instant variety in a field near Greenwich, N.J., has been found to be consistently similar in the vicinity of New Brunswick, N.J.

Figure 1:
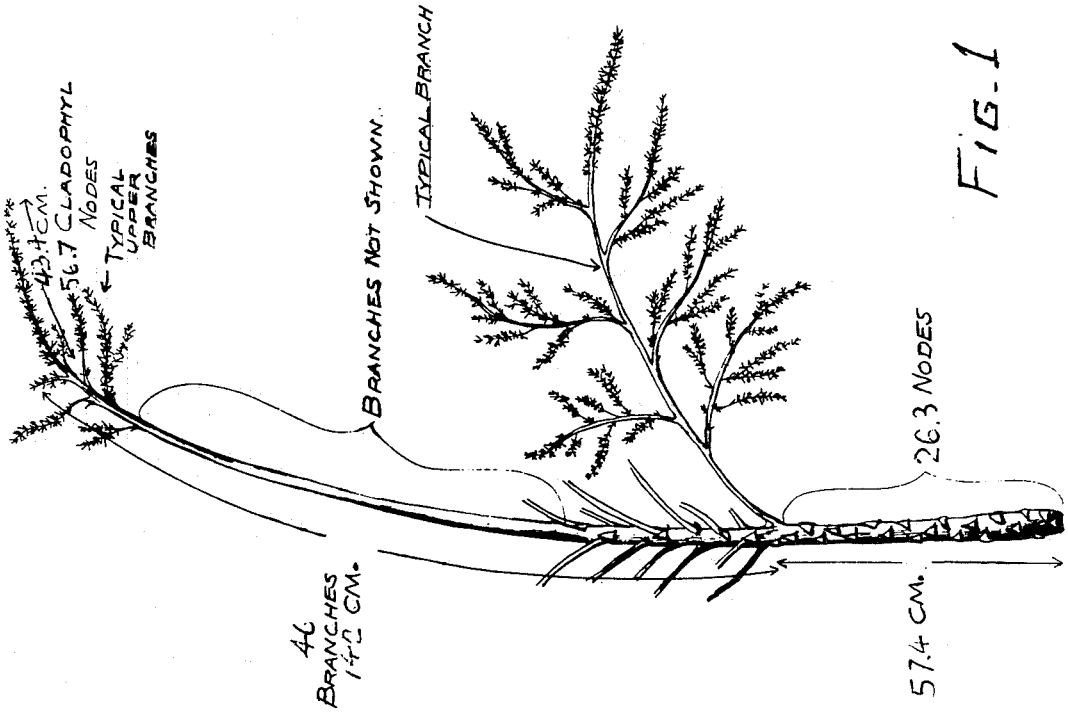

In the accompanying drawing we have disclosed in FIG. 1 a typical stalk of our new variety with certain of the dimensions and other elements directly indicated in black and white.

Figure 2:
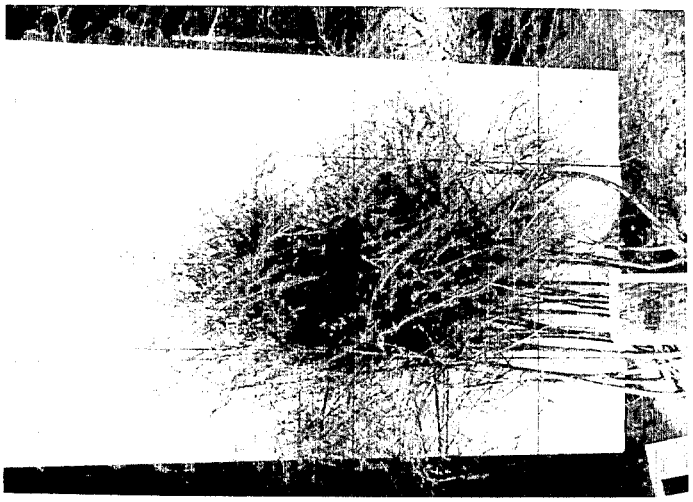

In FIG. 2, we have shown in color as nearly as possible representative of a typical plant, one of our new variety, with the color compared by us to the Munsell Limit Color Cascade and in our opinion as nearly accurate as can be reproduced in an illustration of this kind with notations referring thereto, the photo having been taken under normal daylight conditions in the field where grown.

Data which we have accumulated in reference to the instant variety, is summarized in the following table, which sets forth some of the information which enables us to identify the same and compare it with other varieties as well as those with which it has been crossed to produce hybrids such as that known as "Jersey Centennial" the subject of U.S. Plant Pat. No. 4,998.

ASPARAGUS PLANT DATA
ASPARAGUS PLANT NO. 53 FEMALE "INEZ"

| | |
|---|---|
| Stalk Data | |
| Number of nodes below first branch | 26.3 |
| Number of cm from crown to first branch | 57.4 |
| Number of branches | 46 |
| Number cm between first and last branch | 142 |
| Internode length in cm between branches | 3.1 |
| Number of cladophyll nodes beyond last branch | 56.7 |
| Number of cm beyond last branch | 43.4 |
| Internode length in cm beyond last branch | 0.77 |
| Largest stalk diameter in mm | 21.4 |
| Mean diameter of three largest stalks in mm | 20.8 |
| Number of stalks | 26 |
| Stalk vigor index (No. × (Mean diam.)$^2$) | 11,249 |
| Mature stalk color, bloom removed. | 22–11.5 |
| Color No. (1) | |
| Flow Data | |
| Petal tip (yellow) Color No. (1) | 25–4 |
| Petal base (green) Color No. (1) | 21–9 |
| Flower length in mm | 4.9 |
| Flower width at midpoint in mm | 2.5 |
| Fruit Data | |
| Weight of 100 fruit (g) | 32.6 |
| Water displacement of 100 fruit (ml) | 34 |
| Number of seed per 100 fruit | 408 |
| Weight of seed per 100 fruit (g) | 8.5 |
| Water displacement of seed of 100 fruit (ml) | 10.0 |
| Mature fruit | 33–12 |
| Cladophyll Data | |
| Number per node | 2.54 |
| Length (mm) | 10.74 |
| Width (mm) | 0.151 |

(1) Color number, Munsell Limit Color Cascade, Munsell Color, Macbeth Color and Photometry Division, 2441 Calvert Street Baltimore, MD 21218

The data disclose that the largest stalk is 21.4 mm in diameter and the mean diameter of the three largest stalks is 20.8 mm, the number of stalks averaging 26.

The stalk vigor index (No. X (Mean diam.)$^2$) is somewhat less than others we have developed being on the order of 11,249.

We claim:

1. A new and distinct variety of Asparagus Plant as herein shown and described, distinguished particularly as to novelty by its unique combination of predominately female characteristics, which transmit high yield, resistance to rust (*Puccinia asparagi*), tolerance to root and crown rot (*Fusarium oxysporum*) and (*F. moniliforme*), maintaining vigor through long life, enabling growth of hybrids where standard susceptible cultivars cannot be grown profitably.

* * * * *